United States Patent [19]

Wilson et al.

[11] Patent Number: 5,698,767
[45] Date of Patent: Dec. 16, 1997

[54] HUMAN IMMUNE SYSTEM IN NON-HUMAN ANIMAL

[75] Inventors: Darcy B. Wilson, La Jolla; Donald E. Mosier, Del Mar, both of Calif.

[73] Assignee: Lidak Pharmaceuticals, La Jolla, Calif.

[21] Appl. No.: 543,449

[22] Filed: Oct. 16, 1995

Related U.S. Application Data

[63] Continuation of Ser. No. 57,006, May 4, 1993, Pat. No. 5,476,996, which is a continuation of Ser. No. 425,047, Oct. 23, 1989, abandoned, which is a continuation-in-part of Ser. No. 241,590, Sep. 8, 1988, abandoned, which is a continuation-in-part of Ser. No. 207,273, Jun. 14, 1988, abandoned.

[51] Int. Cl.$^6$ .......................... A61K 35/00; A61K 48/00; C12N 15/00
[52] U.S. Cl. .................. 800/2; 800/DIG. 2; 800/DIG. 5; 424/93.71; 424/93.7; 424/93.1; 424/9.1; 424/534; 424/577; 424/578; 435/325
[58] Field of Search ........................... 800/2, DIG. 2, 800/DIG. 5; 424/93.71, 93.7, 93.1, 9.1, 534, 577, 578; 435/240.2, 325

[56] References Cited

U.S. PATENT DOCUMENTS 4,624,917 11/1986 Sugimoto.

OTHER PUBLICATIONS

Bosma et al., "A severe combined immunodeficiency mutation in the mouse", Nature 301: 527–530 (1983).
Cannon et al., "Epstein–Barr virus induces aggressive lymphoproliferative disorders of human B cell origin in SCID–hu chimeric mice", J. Clin. Invest. 85(4): 1333–1337 (1990).
Custer, R.P. "Severe combined immunodeficiency in the mouse pathology reconstitution neoplasms", Am. J. Pathol. 120(3): 464–477 (1985).
Czitrom et al., "The function of antigen–presenting cells in mice with severe combined immunodeficiency". Immunol. 134(4): 2276–2280 (1985).
Dorshkind et al., "Functional status of cells from lymphoid and myeloid tissues in mice with severe combined immunodeficiency disease", J. Immunol. 132: 1804–1808 (1984).
Dorshkind et al., "Natural killer cells are present in mice with severe combined immunodeficiency", J. Immunol. 134: 3798–3801 (1985).
Dorshkind et al., "Lymphoid bone marrow cultures can reconstitute heterogeneous B and T cell–dependent responses in severe combined immunodeficiency mice", J. Immunol. 137: 3457–3463 (1986).
Garcia et al., "B–cell lymphoma in severe combined immunodeficiency not associated with the Epstein–Barr virus", Cancer 60: 2941–2947 (1987).
Kersey et al., "Relationship of immunodeficiency to lymphoid malignancy", Pediatric Infect. Dis. J. 7(31): S10–S12 (1988).

Lauzon et al., "An expanded population of natural killer cells in mice with severe combined immunodeficiency lack rearrangement and expression of T cell receptor genes", J. Exp. Med. 164(5): 1797–1802 (1986).
Louie et al., "Immunodeficiency and the pathogenesis of non–Hodgkin's lymphoma", Seminars in Oncology 7(3): 267–284 (1980).
McCune et al., "The SCID–hu mouse: Murine model for the analysis of human hematolymphoid differentiation and function", Science 241: 1632–1639 (1988).
Mosier et al., "Transfer of a functional human immune system to mice with severe combined immunodeficiency", Nature 335: 256–259 (1988).
Mosier, D.E., J. Clin. Immunol. "Immunodeficient mice xenografted with human lymphoid cells: New models for in vivo studies of human immunobiology and infectious diseases", J. Clin. Immunol. 10: 185–191.
Namikawa et al., "Infection of the SCID–hu mouse by HIV–1", Science 242: 1684–1686 (1988).
Perryman et al., "Evaluation of fetal liver cell transplantation for immuno–reconstitution", Clin. Immunol. Immunopath. 23(1): 1–9 (1982).
Pinkert et al., "Tissue-specific, inducible and functional expression of the E$\alpha^d$ MHC class II gene in transgenic mice", The EMBO J. 4: 2225–2230 (1985).
Polmar et al., "Long–term immunological reconstitution by peripheral blood leukocytes in severe combined immune deficiency disease", Clin. Exp. Immunol. 64: 518–525 (1986).
Reddy et al., "Human lung tumor growth established in the lung and subcutaneous tissue of mice with severe combined immunodeficiency", Cancer Res. 47: 2456–2460 (1987).
Saxon et al., "Limited B cell repertoire in severe combined immunodeficiency mice engrafted with peripheral blood mononuclear cells derived from immunodeficient or normal humans", J. Clin. Invest. 87: 658–665 (1991).
Shearer et al., "Epstein–Barr virus–associated B–cell proliferations of diverse clonal origins after bone marrow transplantation in a 12-year-old patient with severe combined immunodeficiency", N. Engl. J. Med. 312: 1151–1159 (1985).
Wade et al., "Characterization of xenogeneic mouse–to–rat bone marrow chimeras. I. Examination of hematologic and immunologic function", Transplantation 44(1): 88–92 (1987).
Ware et al., "Human, rat or mouse hybridomas secrete high levels of monoclonal antibodies following transplantation into mice with severe combined immunodeficiency disease (SCID)", J. Immunol. Meth. 85: 353–361 (1985).

Primary Examiner—Jasemine C. Chambers
Assistant Examiner—Jill Schmuck
Attorney, Agent, or Firm—Knobbe, Martens, Olson & Bear, LLP

[57] ABSTRACT

Laboratory non-human animals in which the immune system of a donor is induced in and thrives in vivo and expresses the immune response of the donor animal in a recipient non-human animal of a different species than the donor, and wherein malignant immune system cells of the donor can be induced in the recipient non-human animal by injection of non-malignant donor into the recipient are disclosed.

11 Claims, 5 Drawing Sheets

HUMAN IMMUNE SYSTEM IN NON-HUMAN ANIMAL

This is a continuation of application Ser. No. 08/057,006, filed May 4, 1993, now U.S. Pat. No. 5,476,996, which is a continuation of Ser. No. 07/425,047, filed Oct. 23, 1989, abandoned, which is a continuation-in-part of Ser. No. 07/241,590, filed Sep. 8, 1988, abandoned, which is a continuation-in-part of Ser. No. 07/207,273, filed Jun. 14, 1988, abandoned, to which priority is claimed.

FIELD OF THE INVENTION

This invention relates to immunology and to oncology. Specifically, the invention relates to the generation of a functional human immune system in living laboratory animals, and to the selective induction of malignancy in human lymphocytes while contained in living laboratory animals.

BACKGROUND OF THE INVENTION

The human immune system is an elegant and complex system which protects the human body from foreign molecules and organisms; it also greatly limits the efficacy of otherwise life-saving organ transplants. The immune system is the organic system in the body which is badly damaged by acquired immunodeficiency syndrome (AIDS). The immune system may marshall armies of cells to ward off infection and/or induce responses which range from the inconvenient to the disabling.

The general sequence of the various immune responses, the cells and molecules involved, and certain of the immune response modulating factors are now generally understood, but much remains to be learned respecting specific cells, enhancing and suppressing factors, and the regulation of the immune response.

The immune response includes several molecules and cells which act, to greater or lesser degrees, to interdict immunogenic agents, typically allergens or pathogens, and/or to build a defense system to the particular immunogenic pathogen. Neutrophils, produced in the bone marrow, scavenge foreign molecules and organisms which carry antigenic determinants, and the complement system may attach to the invading foreign species. Macrophages also engulf foreign molecules and cells, as well as debris from the body's own cells, and display the antigenic determinants of the invader thus signalling other cellular constituents of the immune system to respond.

T cells carry an array of receptors which recognize certain specific antigens, and the T cell system generally constitutes one of the key constituents of the overall immune system. There are three basic classes of T cells, referred to as Helper T cells, Suppressor T cells and Killer T cells. Helper T cells are activated to reproduce by a protein released by the macrophage, interleukin-1, It-1, and they produce a variety of interleukins which activate other T Cells and B cells. Killer T cells attack and destroy certain immunogenic cells such as tissue from foreign sources, parasites, and immunogen containing cells such as virus-infected cells. Suppressor T cells modulate the immune response to meet the challenge from the foreign invader without an over-response.

B cells, stimulated by T cells, produce antibodies which couple very specifically to the antigenic determinants of the invading species. Antibodies coupled to the antigen inactivate the antigen bearing cell and/or makes it more vulnerable to ingestion or destruction by macrophages, neutrophils, and other elements of the immune system, and they activate the complement system to increase the attack upon the invading species. Both B cells and T cells contribute to a residual immunity to the particular antigen which may last for a few weeks or a life time.

The present invention contemplates the transfer of the critical functions of the immune response system described generally described above from a human, or one animal, to a mouse or a laboratory animal of a different species by the transfer and in vivo nurturing of cells of organs or fluids which express the immune function. The two main cell types involved in vertebrate immunity are phagocytes and lymphocytes. Phagocytic cells are sometimes referred to as the reticuloendothelial system, and more recently as the mononuclear phagocyte system, while lymphocytes, their precursors, derivatives and supportive cells are referred to as the lymphoid system. Cells from these systems may be used in the transfer of the immune functional system from the human, or other donor species, to a SCID mouse, SCID horse, or other laboratory animal, different from the donor species whose immune system is to be studied. The mononuclear phagocyte system, (MPS), includes cells involved in defense-related phagocytesis derived from bone marrow precursor cells characterized by involvement of immunoglobulins and serum complement. The organs in which most MPS cells are localized are the bone marrow, peripheral blood, connective tissue, liver, lungs, lymph nodes, spleen and nervous system.

The lymphoid system comprises the tissues and organs in which lymphocyte precursors and their derivatives originate, mature, lodge and are moved. The principal organs of the lymphoid system of an adult human are, in addition to the lymphatic and blood vessels, the thymus, spleen, bone marrow, the lymphatic nodes, e.g. cervical, axillary, lumbar, iliac and inguinal nodes, and to a lesser extent the heart and stomach. The fetal lymphoid system includes the yolk sac, pharyngeal pouches, bone marrow, liver, spleen and thymus.

The present invention may involve the transfer of cells of any of or more than one of the above organs of the immune system.

Among the goals and features of the present invention is the evaluation of drugs, the development of therapeutic materials, the development of immunizing compositions, and the general study of methods for preventing, treating, enhancing or suppressing immune response to various foreign materials which are or may become pathogenic or undesirable in humans, or other donor species whose immune system is to be studied. An important application of this principle is the development of vaccines and treatments for pathogenic organisms. The antigenic determinants of some pathogenic organisms remain constant from generation to generation and it is possible to induce immunity to diseases caused by such organisms; indeed, by vaccination many of the diseases which ravaged the world in past centuries have been essentially eliminated as a threat to the earth's human population. Other organisms, such as influenza virus, however, mutate rapidly and/or are not single species but, rather, constitute a large number of species which differ immunologically. A vaccine to a single form of such species does not induce a lasting immunity to all forms of the species.

Successful development of vaccines and therapeutics for organisms and materials which trigger the immune response requires the ability to track the immune response upon challenge by such organisms and materials. It is, in most instances, possible to track the human immune response in several ways, more or less completely. The most complete tracking of the immune response would, theoretically, be possible in the human body, where the entire immune system resides. This is not generally convenient, however, even under the best of circumstances, where the invading species is not fatal, because it is generally impractical to use the human body as an immune system host for long term studies. It is, therefore, common practice to use in vitro cultures of human cells for studies of the human immune system. This approach, however, has limitations; several features of the complex immune system do not function well in culture. Another approach is to study and/or the immune system of other species, mice, rats or guinea pigs typically.

It would be a great step forward in the study of the human immune system to have available a laboratory animal which could be husbanded in a controlled environment and which would provide an adequate in vive host for the human immune system. One of the important features of this invention is the development of just such a laboratory animal, examples of which SCID animals, e.g. mice, in which the essential elements of the human immune system resides and thus produces human antibodies when challenged with particular immunogens.

One particular example where the availability of a functioning human immune system in mice, or another laboratory animal, would be a major advantage is in AIDS research. Currently, the most difficult challenge to immunologists has come with the spread of the Human Immunodeficiency Virus, HIV, (also referred to, generally in earlier reports, as lymphadenopathy-associated virus, LAV, and human-T-lymphotropic virus, HTLV, and acquired immune deficiency syndrome (AIDS) related virus, ARV) which is generally recognized as causing acquired immunodeficiency syndrome AIDS. At least two HIV viruses, HIV-1 and HIV-2, have been identified as AIDS infective agents. These retroviruses, in which the genetic material is RNA rather than DNA, carry an enzyme which catalyzes transcription of vital RNA into DNA in the host. The DNA may then be integrated into the genome of an infected cell where it can then be inherited by daughter cells and form new virus particles. Through mechanisms not fully understood in humans, the HIV virus disrupts the normal immune response by depleting T helper/inducer cells, specifically T4 or CD4$^+$ cells, which are responsible for the induction of most, if not all, of the functions of the human immune system. One of the first and ultimately most lethal events in the progress of AIDS is the suppression of much or all of the human immune system, leaving the body with little or no defense against the constant attack upon the human body by bacteria, viruses, plant and animal produced antigens, chemicals and foreign materials generally.

The study of the immunology of HIV is more challenging than the study of more traditional immunogenic materials for several reasons. All, or nearly all, of those in whom HIV induces the AIDS set of symptoms die within one to two years and are susceptible to most infectious organisms which are of little threat to those with a normally functioning immune system. Thus, the human body which is, at best, a very unsatisfactory in vivo host for immunological studies, is even less suitable for studying the HIV. Add to these factors the latency exhibited by HIV in inducing AIDS symptoms, the low proportion of lymphocytes even in fully infected AIDS patients which contain HIV (1:10,000 to 1:100,000), the possibility that HIV induces an autoimmune response, and the probable induction by HIV of an autoantibody which reacts with surface protein on HIV-infected T4 cells, suppressing the proliferation of T4 cells and inducing cytotoxicity of T4 cells, and it becomes apparent that the human body is not a suitable subject for most immunological studies on HIV. In addition, testing of trial drugs on AIDS patients or HIV vaccines on healthy patients carries risk factors which may make such studies unethical in man.

There has, of course, been an enormous amount of work done on the immunology of HIV and on methods for detecting the virus. For example, a diagnostic method for AIDS and pre-AIDS, and a kit therefor involving the formation of an antigen-antibody complex has been described by Axler-Blin, et al., U.S. Pat. No. 4,708,818. Virus are isolated from the sera of patients afflicted with lymphadenopathy syndrome (LAS) or AIDS. Immunodeficiency virus (HIV), vital extract, structural proteins and other fractions of the retrovirus are recognized by the sera of such patients.

The human immune system responds directly or indirectly the introduction of substances foreign to the human body into the human body by injection, ingestion or otherwise. Some such responses are not immunological, in the strictest sense, but the responses which appear in the immune system may be used as indicative of the efficacy or toxicity of the foreign substance. In the evaluation of new drugs it has been necessary to test the drug in three, or sometimes more, species, including in many cases in primates, before the drug could be considered for testing on humans. One of the features of this invention is that a relatively inexpensive test animal is made available for testing the response of the human immune system to substances foreign to the human without having to subject humans to such testing.

In the exemplary embodiment of the present invention, the cellular components of the human immune system are injected into a mutant strain of mice; these mice have severe combined immunodeficiency disease (SCID), are well-known and widely used laboratory animals, and have been used in many immunological and oncological studies, see, for example, Dorshkind K., et at., "Functional Status of Cells from Lymphoid and Myeloid Tissues in Mice with Severe Combined Immunodeficiency Disease," *J. Immunol.*, 132(4): 1804–1808, 1984; Czitrom, A. A., et al., "The Function of Antigen-Presenting Cells in Mice with Severe Combined Immunodeficiency," *Immunol.*, 134(4):2276–2280, 1985; Dorshkind, K. et al., "Natural Killer Cells are Present in Mice with Severe Combined Immunodeficiency," *J. Immunol.*, 134(6):3798–3801, 1985; Custer, R. P., "Severe Combined Immunodeficiency in the Mouse Pathology Reconstitution Neoplasms," *Am. J. Pathol*, 120(3):464–477, 1985; Ware, C. F., "Human Rat or Mouse Hybridomas Secret High Levels of Monoclonal Antibodies Following Transplantation into Mice with Severe Combined Immunodeficiency Disease," *J. Immunol. Methods*, 85(2):353–362, 1985. The latter publication reports the investigation of mice with severe combined immunodeficiency disease (SCID) for their ability to grow xenogeneic hybridomas of mouse, rat and human origin. Two rat x mouse hybridoma lines (187.1.10 and 3B9) and one mouse x mouse hybridoma (2D9) grown (as ascites tumors) in pristane-treated SCID mice as ascites tumors showed a 100–200-fold increase in monoclonal antibody levels over the amount produced in vitro with a total yield up to 0.5 g of antibody per animal. A human x human hybridoma, CLL-11-D I, exhibited a 1000-fold increase in human immunoglobulin levels in ascites (1.3 mg/ml) as compared to that obtained in tissue culture.

Mice with severe combined immunodeficiency syndrome (SCID) exhibit an impairment in both T and B cell maturation, Lauzon, R. J., et al., "An Expanded Population of Natural Killer Cells in Mice with Severe Combined Immunodeficiency Lack Rearrangement and Expression of T Cell Receptor Genes," *J. Exp. Med.*, 164(5): 1797–1802, 1986; Dorshind, K. et al., "Lymphoid Bone Marrow Cultures can Reconstitute Heterogenous B and T Cell-Dependent Responses in Severe Combined Immunedeficient Mice," *J. Immunol.*, 137(11):3457–3463, 1986.

Other laboratory animals which possess little or no immune system of their own, or which have been treated with drugs or radiation, or produced through traditional genetic development or genetic engineering to have either a suppressed immune system, a weakened immune system or a modified immune system, or no immune system at all, such as, e.g. SCID horses and other SCID animals and potentially even AIDS infected animals in which AIDS has been arrested after destruction or inactivation of the animals' immune system may be considered as laboratory animal candidates for use in the present invention and thus functionally the same as or equivalent to SCID animals. A number of such animals are known, e.g. SCID mice, SCID horses, nude mice, etc., and equivalent animal candidates will undoubtedly come available as needed. SCID horses, for example, have been widely studied, see e.g. Perryman L. E., McGuire, T. C., Torbeck, R. L., and Magnuson, N. S., "Evaluation of Fetal Liver Cell Transplantation for Immuno-Reconstitution," *Clin. Immunol. Immunopath.*, 23(1):1–9, 1982. Perryman, et at., ibid., report, for example, on efforts to transfer the immune system from a normal horse to an SCID horse in which fourteen foals with severe combined immunodeficiency (SCID) were given single-cell suspensions prepared from livers of equine fetuses at 45–201 days gestational age. None of the foals demonstrated functional engraftment in terms of identifiable donor lymphocytes, increased peripheral blood lymphocyte counts, development of phytolectin- or antigen-responsive lymphocytes, or the ability to synthesize Ig and specific antibodies. Such a transfer of at least part of the immunological system was, previously, apparently transferred within the same species using this technique employing fetal liver and thymus cells in combination. No transfer of the immunological system of one species to another species is known to have been reported.

Another need for a model where the cellular components of a human immune system can be made to function in mice, or other laboratory animals, is for studies of tumors and oncegenesis involving the human immune system. Malignancies can be induced in laboratory animals by the implantation of malignant cells or by exposing the animal to carcinogens. In the first instance, the type of malignant cell implanted defines the malignancy and in the second instance the nature of the malignancy to be expected is principally a function of the point of exposure of the animal to the carcinogen. For example, SCID mice have been used to propagate a human lung tumor, Reddy, S., et al., "Human Lung Tumor Growth Established in the Lung and Subcutaneous Tissue of Mice with Severe Combined Immunodeficiency," *Cancer Res.*, 47(9):2456–2460, 1987. Thus, a feature of the present invention is that under certain conditions, malignancy of human lymphocytes can be induced within a relatively short period of time, within about eight weeks, thus providing a rapid and attractive model for the study of malignant transformation of human lymphocytes.

SUMMARY OF THE INVENTION

The following abbreviations, used in this summary and throughout the specification, have the following meanings:

| | |
|---|---|
| AIDS = | acquired immunodeficiency syndrome |
| Con A = | concanavalin A, a mitogen that stimulates proliferation of human T cells. |
| DNA = | deoxyribonucleic acid, the genetic material of almost all forms of life except retroviruses. |
| ELISA = | enzyme linked immunoabsorbent assay, in this case an assay for human antibody. |
| GVH = | graft-versus-host disease, a condition that may follow injection of functional T cells into an immunodeficient host. |
| i.v. = | intravenous injection route. |
| i.p. = | intraperitoneal injection route. |
| MHC = | major histocompatibility complex, the genetic region encoding cell surface molecules critical for T lymphocyte recognition of foreign antigens. |
| MLR = | mixed lymphocyte reaction, the proliferation of T lymphocytes that follows stimulation with cells from an individual with a different MHC. In the case of humans, T cells from any two individuals with the exception of identical twins will react in the MLR. |
| MPS = | Mononuclear phagocyte system, including stem cells, precursor cells, monocytes and macrophages, and the organs in which such cells are localized, e.g. bone marrow, peripheral blood, connective tissue, liver, lungs, lymph nodes, spleen and nervous system. |
| Mφ= | Macrophage(s). |
| PBL = | peripheral blood leukocytes, in this case from humans. |
| PWM = | pokeweed mitogen, a stimulus for the proliferation of human T and B cells. |
| TNP-TT = | trinitrophenyl-tetanus toxoid, a simple chemical coupled to a protein to which most humans have been immunized. |
| SCID = | Severe Combined Immunodeficiency. In reference to animals, e.g. mice, horses, etc. the term SCID usually denotes animals which hereditarily possess no immune system or a severely deficient or impaired immune system, but, as used here, would include animals which had been treated or resulted from genetic manipulation which did not possess an effective immune system and which, therefore, could host in vivo the immune system of another animal. |

The pressing need for a better experimental system for AIDS research has brought into sharp focus the shortcomings of available animal models and the practical and ethical limitations of studies of immune responses and vital pathogenesis in humans ("News and Views," *Nature*, 333:699, 1988; Zagury, D. et al., *Nature*, 332:728, 1988). Current studies of the human immune responses are limited to: (1) relatively restrictive in vivo experiments; and (2) several in vitro systems that, while useful, allow only short term studies and support responses to only a few antigens (*Immunological Reviews*, 45:1–275, 1979). Neither model is particularly amenable to studies of the pathogenesis of diseases of the immune system.

According to the present invention, mice with severe combined immunodeficiency (C.B.-17 scid, hereinafter SCID) accept xenografts of adult human peripheral blood leukocytes (PBL). The transplanted human PBL expand in number and survive for at least 15 months and have been shown to reconstitute human immune function at both the T and B cell level. Human immunoglobulin production is restored, and secondary antibody responses to antigens such as tetanus toxoid can be induced. Thus, the present invention provides a novel experimental immune system in which human peripheral blood leukocytes (PBL) reconstitute immunologic function in mice with severe combined immunodeficiency (SCID) (Bosma, G. C., Custer, R. P. and Bosma, M. J., *Nature*, 301:527, 1983).

PBL transplanted in SCID mice increase in number for at least fifteen months and all reconstituted mice show spontaneous secretion of human immunoglobulin. PBL reconstituted SCID mice produce a specific human antibody response upon immunization. All of the major cell populations present in PBL are found in the lymphoid tissue and blood of SCID recipients.

Mice transplanted with $50 \times 10^6$ or more PBL from Epstein-Barr virus (EBV) seropositive donors develop EBV-positive B cell lymphomas at 8 to 16 weeks after PBL engraftment, whereas mice reconstituted with PBL from EBV-seronegative donors fail to develop tumors. These tumors involve both lymphatic and non-lymphatic organs, and histologically resemble poorly differentiated immunoblastic lymphomas. The tumors are associated with high levels of human immunoglobulin secretion and serum electrophoresis reveals oligoclonal immunoglobulin banding patters. Analysis of tumor DNA shows the presence of EBV genomes and oligoclonal patterns of immunoglobulin $J_H$ gene rearrangement. Taken together, these observations indicated an EBV-related proliferation of B lymphocytes leading to the rapid appearance of oligoclonal B cell malignancies following transfer of B lymphocytes from "normal" donors to SCID mice.

SCID mice reconstituted with PBL from EBV-seronegative donors have been infected with the LAV-1 strain of human immunodeficiency virus (HIV-1). Virus has been recovered by co-culture with T lymphoblasts from most infected animals, and the virus recovery has increased with time after infection. Some mice with high virus tilers have developed an acute wasting syndrome and depletion of human T cells. Mice injected with virus-infected syngeneic T cell blasts have shown more rapid progression of the disease than mice infected with free HIV. Thus, HIV-infected human PBL-reconstituted SCID mice are now available as small animal models in AIDS research.

Injection of fewer PBL from EBV-positive donors or use of PBL from EBV-negative donors results in stable long-term reconstitution of a functional human immune system in all SCID recipients. This xenogeneic transplantation of human lymphoid cells provides a useful model for the study of normal human immune function, the response of the immune system to pathogenic agents, early events in lymphomagenesis, and for the study of certain aspects of the response of the human immune system from any substance foreign to humans, e.g. in the evaluation of drugs for efficacy and side effects and in the evaluation of materials for possible toxicity to human beings.

SCID mice, by virtue of their immunodeficiency, are known to be permissive for the growth of transformed human cell lines, (Ware, C., Donate, N. and Dorshkind, K., *J. Immunol. Methods*, 85:353, 1985; Reddy, S. et al., *Cancer Res.*, 47:2456, 1987), but it was not heretofore known that SCID mice had the ability to support the survival of normal, mature lymphoid populations.

The present invention is founded upon two important discoveries.

First, it was discovered that the immune system of a donor animal can be created in vive in a recipient animal of a different species than that of the donor animal. This is accomplished by injecting donor animal cells of myelocytic or lymphocytic lineage capable of developing immune functions of such donor animal into a living recipient animal of a different species which has a severely deficient immune system or lacks a functioning immune system. These injected cells maintain the recipient animal alive and develop an immune system in the recipient animal which exhibits the donor's immune response characteristics. For example, one can transfer cells of the immune system organs of a human, or other donor animal, e.g. human leukocytes, to SCID animals, e.g. SCID mice, and later (two weeks, for example) stimulate those cells to produce, in vivo, a human antibody response, indicating that all essential components of the human immune system are able to function in the environment of the SCID animal. This model system will be useful for the study of normal and abnormal human immune functions.

Secondly, it was discovered that malignancies in immune system cells of one species can be induced and studied in another species by injecting non-malignant immune system cells of a donor animal into a recipient animal of a different species, maintaining the recipient animal alive for from about eight weeks or longer and studying malignant human immune system cells in or derived from the recipient animal. For example, SCID animals, e.g. mice, injected with normal, non-malignant cells of the immune system of a human or animal donor, e.g. human leukocytes, are highly prone to the development of human immune cell malignancies, e.g. lymphocyte malignancy, within about eight to sixteen weeks. This may in some, but not all, circumstances involve latent infection of the donor leukocytes with Epstein-Barr Virus (EBV). Thus, a rapid and attractive model for the study of malignant transformation of normal human lymphocytes has been invented.

In one embodiment, the invention is a method for producing a continuing supply of malignant cells of the immune system of a donor by introducing non-malignant cells of the immune system of the donor into an immune deficient recipient animal of a species different from the donor and nurturing the recipient animal for from about eight weeks or longer to cause malignant cells of the donor to proliferate In vivo in the recipient animal.

In a living embodiment, the invention comprises a mouse which hosts malignant human immune cells induced in vivo, the malignant cells being induced in such mouse by injection of non-malignant human immune system cells into the mouse.

In another living embodiment, the invention comprises a mouse hosting the essential elements of the human immune system, namely human macrophages, T lymphocytes, and B lymphocytes, which exhibit a human immune response.

In one important living embodiment, the invention is a SCID animal, e.g. a SCID mouse comprising a reconstituted human immune system, which, in addition to comprising the essential elements of the human immune system, comprises human MHC (Class II) restricting antigens for priming the human immune response. Such Class II antigens may be introduced by implantation and reconstitution as described herein, or by mating SCID mice to transgenic mice which carry human Class II genes prior to implantation of human immune systems.

In another embodiment, the invention is a method of studying cells of the immune system of a human by injecting human cells myelocytic, lymphocytic, or erythrocytic lineage into an immune deficient animal and studying human immune system cells in the animal. The injection is preferably intraperitoneal, and the preferred cells are leukocytic components of peripheral blood.

In a similar embodiment, the invention is a method for studying malignancies in human immune system cells by injecting non-malignant human immune system cells into the animal, maintaining the animal alive for about eight weeks or longer and studying malignant human immune system cells in or derived from the animal. Again, the injection is preferably intraperitoneal, and one preferred source or cells are the leukocytic components of peripheral blood; a particularly preferred source of such cells being from an EBV⁺ human donor.

In a more general sense, the invention is a method of studying the immune system of a donor animal comprising the steps of injecting donor animal cells of myelocytic, erythrocytic or lymphocytic lineage capable of developing immune functions of such donor animal into a living recipient animal which has a severely deficient immune system or lacks a functioning immune system and maintaining the recipient animal alive for a period of from about two or more weeks sufficient for the donor immune cells to develop an immune system in the recipient animal which exhibits the donor's immune response characteristics. A preferred recipient animal is an immunodeficient nude.xid.beige mouse.

The invention is also embodied in a method of preparing a laboratory animal for studying the immune system of a donor animal by injecting donor animal cells of myelocytic, erythrocytic or lymphocytic lineage capable of developing the donor's immune function into a living a laboratory animal of a different species than the donor species which recipient animal has a severely deficient immune system or lacks a functioning immune system and maintaining the said laboratory animal alive for a period of about two or more weeks sufficient for the donor immune cells to propagate in vivo and develop an immune system in the said laboratory animal which exhibits the donor's immune response characteristics, and in a laboratory animal produced in accordance with such method.

The invention may also be regarded as an improvement in the study of cells of the immune system of a first species of animals, wherein such cells are produced in vivo in a second species of animal by injecting into the second species lymphocytic, myelocytic or erythrocytic lineage cells of the first species which are capable of or can develop the capability of expressing the immune functions of the first species therein, keeping the second species of animal alive for at least one to two weeks, and studying the immune system cells of the first species in or derived from the second species.

In one preferred application and embodiment, the invention is embodied in a method of studying cells or the immune system of a human by creating a laboratory animal by injecting non-malignant cells of organs of the human immune system into an SCID animal, keeping the animal alive for about two weeks or more to permit human immune cells to proliferate in vivo in the recipient laboratory animal, challenging human immune-type cells in the animal with a substance which is known to induce or suspected of inducing an immune response in humans or modifying the immune cells in humans and studying the immune response and/the immune system cells in or harvested from the recipient animal. The human immune system cells, such as lymphocytic, myelocytic and erythrocytic lineage which are capable of developing immune functions, are preferably injected into the animal intraperitoneally and may comprise lymphocytes, e.g. B lymphocytes or peripheral blood lymphocytes.

Another feature of the invention is embodied in a method for studying malignancies in the cells of organs of the human immune system comprising treating SCID animals by injecting non-malignant cells of such organs of the human immune system into the recipient animal, maintaining the recipient animal alive for from about eight to about sixteen weeks or longer and studying malignant cells of such organ of the human immune system in the recipient animal. The injection is preferably given intraperitoneally, and immune system cells are preferably human peripheral blood lymphocytes, which may be from an EBV⁺ human donor.

The invention comprises methods for studying immunologically related diseases such as, for example, acquired immunodeficiency disease. In this exemplary study, the invention comprises creating a laboratory animal by injecting human cells of myelocytic, erythrocytic or lymphocytic lineage capable of developing the human immune function into a non-human SCID animal, keeping the animal alive for about eight weeks or more to permit such cells to proliferate in vivo in said animal, or the equivalent steps of obtaining such a laboratory animal. At or after about eight weeks, human immunodeficiency virus is introduced into said laboratory animal and, thereafter, the animal and/or the human immunodeficiency virus in or harvested from said animals are studied.

DESCRIPTION OF THE PREFERRED EMBODIMENTS

The following description and the experiments specifically discussed are intended to illustrate two general principles of wide and general application and not to circumscribe the invention. First, the data demonstrate that the critical elements of the human immune system can be shown to function In vive in SCID mice. Secondly, the data demonstrate that human lymphocyte malignancies can be induced reproducibly in SCID mice.

The first principle has general applicability in that laboratory animals in which the human immune system is resident are now available for studying, in vive, the human immune response to virtually any antigenic material. Such a living laboratory for the human immune system has virtually limitless applicability and will be of great value in studying all immune-related responses and diseases, with particular value in studying AIDS and other diseases in which the immune system is disrupted or inactivated.

The second principle has general applicability in oncology, in the screening and evaluation of chemicals and biologicals which may have value in treatment of some forms of human cancer, by providing a living laboratory of malignant cells for study.

With these principles of broad and general applicability in mind, specific experiments and results will be discussed merely as illustrative of the principles involved.

Such a model would provide an important means for approaching questions of the early events in the pathogenesis of AIDS using human cells and HIV, and it would be very useful for vaccine and drug testing programs. The SCID mouse was selected because it is conveniently available, and easily managed as a laboratory animal; however, any animal, of a species different from that in which the immune system of interest normally resides, in which the natural immune system is non-existent or so modified as to permit the in vive acceptance of organs of the immune system of interest, may be considered as a laboratory host model for studying the immune system of interest. Alternative animals for PBL reconstitution include, among others, SCID.beige (scid.bg) mice deficient in T, B, and NK cells, nude.xid.beige (nu.xid.bg) mice deficient in T, B, and NK cells, SCID mice irradiated with 300 rads, SCID.HLA-DQ transgenic mice deficient in T and B cells with mouse antigen presenting cells expressing human class II HLA molecule, and SCID.HLA-DQ mice irradiated with 300 rads.

A series of studies were undertaken to determine whether it would be possible to reconstitute immunologically deficient SCID mice with a functional human immune system. Such a model would provide an important means for approaching questions of the early events in the pathogenesis of AIDS using human cells and HIV, and it would be very useful for vaccine and drug testing programs. The SCID mouse was selected because it is conveniently available, and easily managed as a laboratory animal; however, any animal, of a species different from that in which the immune system of interest normally resides, in which the natural immune system is non-existent or so modified as to permit the in vivo acceptance of organs of the immune system of interest, may be considered as a laboratory host model for studying the immune system of interest. Nude mice, SCID horses, etc. may thus be considered.

Figure 1:
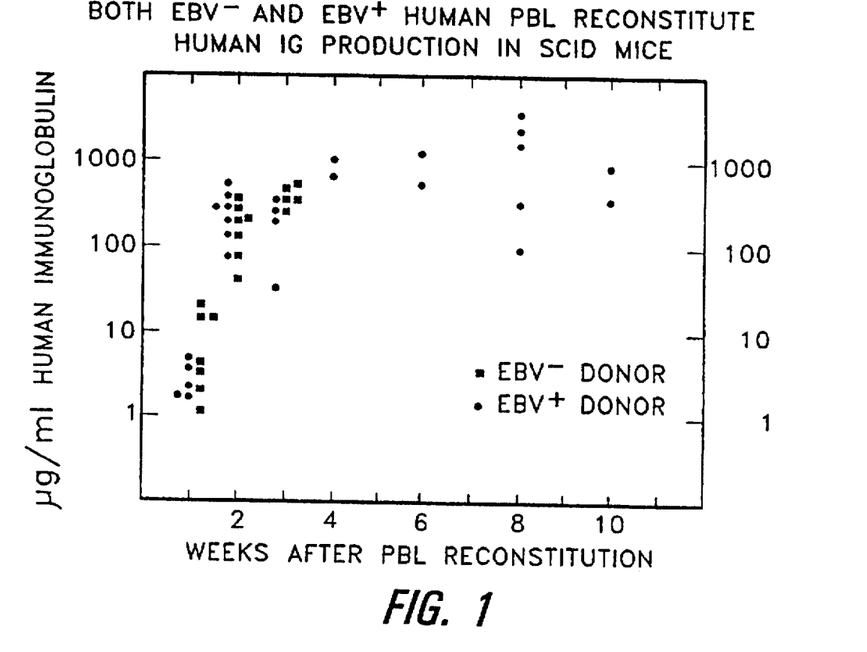
FIG. 1 shows that both EBV-negative and EBV-positive human PBL reconstitute human immunoglobulin production in SCID mice.

Briefly, human PBL ($10^7$–$10^8$) were injected i.v. or i.p. into panels of C.B.-17 SCID mouse recipients previously screened and shown to lack detectable levels of mouse Ig. Mice were bled at weekly intervals and their sera monitored in ELISA assays for levels of human Ig. The results of these assays are depicted in FIG. 1. No clinical evidence of xenogeneic GVH disease was observed, a result which might have been anticipated if human T cells were to respond to mouse MHC antigens. All mice injected i.p. showed detectable tilers of human Ig at one week post grafting and thereafter the levels rose exponentially to 1–4 mg/ml, a level approximately that of normal human serum, and remained at this level for up to twenty-six weeks and remained at this level through the twenty-eighth week.

In a separate experiment, groups of SCID mice were immunized with 100 μg trinitrophenol-tetanus toxoid (TNP-TT) two weeks after reconstitution with human PBL. One and two weeks later, the human antibody response to both TNP and TT as well as the total human immunoglobulin level were determined by ELISA. A substantial antibody response to TT and it weaker response to TNP was induced in two groups of mice reconstituted with PBL from two different donors. The amount of TT-specific antibody accounted for up to 10% of total human immunoglobulin in the best responders. Unimmunized SCID mice reconstituted with human PBL or control SCID mice containing no human PBL failed to produce TNP- or TT-specific antibody. Thus, a fully functional human immune system has been reconstituted in SCID mice, since the antibody response to TNP-TT is known to require the participation of human helper T cells, macrophages and B Cells.

SCID mice injected i.p. with large numbers of normal, non-malignant human PBL have developed lymphoid malignancies in eight to sixteen weeks post-reconstitution. The evidence for malignancy was the gross enlargement of lymphoid organs, the invasion of liver, lung, and kidneys by histologically malignant cells, and the detection of one or a small number of expanded B cell clones by serum electrophoresis and Southern analysis of DNA with human immunoglobulin probes. The human origin of the tumors was confirmed by both the human Jh probe and hybridization with a human specific Alu-sequence probe. Evidence for the ability to transplant these tumors has yet to be obtained, although the tumors can be established as cell lines in tissue culture. This reproducible development of lymphoid malignancies under the appropriate conditions of cell transfer establish the PBL-reconstituted SCID mouse as a powerful model for the study of malignant transformation.

Using the methods of this invention, one can transfer cells of the organs of the human immune system, e.g. human leukocytes, to a laboratory animal of a different species in which such animal's immune system is deficient, absent or so modified as to permit acceptance of another immune system, e.g. SCID mice, and stimulate the thus transferred cells to express the human immune response, producing human antibody, by reason of the presence and functioning of human T and B cells in the laboratory animal. With all the essential components of the human immune system functioning, a new laboratory animal is available which will be useful for the study of normal and abnormal human immune functions.

Experiments were initiated involving transferring varying numbers of PBL by different routes into SCID mice to define conditions that minimized the anticipated GVH reaction. Table 1 summarizes our findings from these experiments.

TABLE 1

SUMMARY OF HUMAN PBL --> SCID TRANSFERS

| Number of PBL Transferred | Donor EBV Status | Route | SCID Recipients Analyzed | Outcome |
|---|---|---|---|---|
| 10–90 × $10^6$ | positive | i.v. | 10 | all recipients alive 16 months post-transfer, no human Ig production, few human lymphoid cells detected, no human tumors |
| 60–90 × $10^6$ | positive | i.p. | 38 | all recipients produce human Ig within 1 week of reconstitution, survival of human T, B, and Mφ documented, produce human antibody response to tetanus toxoid, develop EBV+ B cell lymphomas or lymphoproliferative disease in 8–16 weeks post transfer. |
| 10 × $10^6$ | positive | i.p. | 22 | all recipients produce human Ig within 2–3 weeks of reconstitution, survival of human T, B, |

TABLE 1-continued

SUMMARY OF HUMAN PBL --> SCID TRANSFERS

| Number of PBL Transferred | Donor EBV Status | Route | SCID Recipients Analyzed | Outcome |
|---|---|---|---|---|
| | | | | Mϕ documented, antibody response to tetanus toxoid at 20 weeks post-transfer, all recipients alive at 6–26 weeks post-transfer, no gross evidence of tumors. |
| $50 \times 10^6$ | negative | i.p. | 3 | all recipients produce human Ig within 1 week of reconstitution, documentation of human T, B, Mϕ survival, positive T cell proliferative response to tetanus toxoid in vitro, no gross or microscopic evidence of tumor at 14 weeks post-transfer. |

*an additional 10 SCID recipients were injected with PBL from an EBV-seronegative donor. These recipients developed B lymphomas which hybridized with an EBV-specific DNA prob. This donor is presumed to be EBV virus positive.

Several conclusions are evident: (1) xenogeneic GVH disease was not a significant problem in any recipients, although mild and transient GVH reactions may contribute to spontaneous B cell activation. (2) Survival of human lymphoid cells depended upon intraperitoneal injection of PBL; intravenous injection was ineffective. (3) Both the EBV status of the PBL donor and the number of PBL transferred were critical. Successful establishment and maintenance of functional human lymphoid cells in SCID recipients was achieved with low numbers ($10 \times 10^6$) of PBL from an EBV-positive donor or higher numbers ($50 \times 10^6$) of PBL from an EBV-negative donor. In contrast, transfer of $50 \times 10^6$ or more PBL from an EBV-positive donor resulted in both a rapid reconstitution of human immune function and development of human lymphoid tumors by eight to sixteen weeks after cell transfer in most mice. The tumors that were analyzed in detail were human B cell lymphomas by histologic and immunologic criteria. DNA from these tumors hybridized with probes for EBV as well as human Alu sequences, and serum from tumor-bearing mice showed monoclonal or oligoclonal immunoglobulin patterns.

Figure 2:
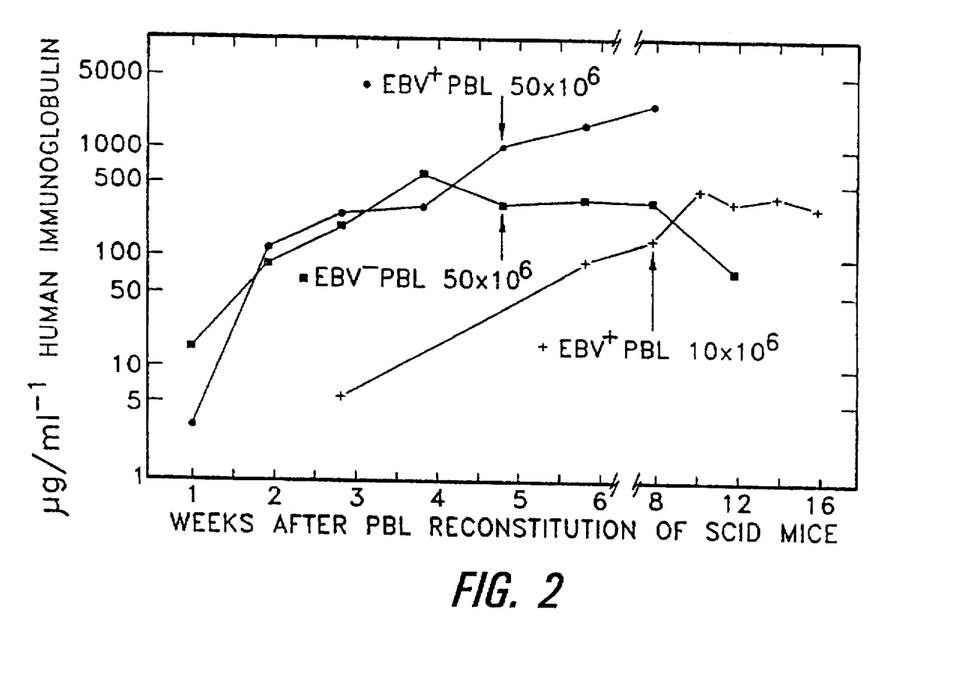
FIG. 2 depicts human immunoglobulin levels at one to sixteen weeks after PBL reconstitution of SCID mice.

Human immunoglobulin (Ig) levels in SCID sera were measured weekly to follow B cell survival and function. FIG. 2 illustrates the outcome in three groups of SCID mice, each injected with PBL from a different donor. Human immunoglobulin (Ig) levels in the serum of SCID mice at intervals of time following intraperitoneal injections of human peripheral blood leukocytes (PBL). Methods: PBL from Epstein-Barr virus (EBV) seropositive and seronegative donors were prepared by Ficoll-Hypaque separation. Sterile PBL suspensions were injected i.p. into eight- to ten-week-old C.B-17 SCID mice previously shown not to produce mouse Ig (10% of SCID mice secrete some mouse Ig; no such mice were used in these experiments). Human Ig was quantitated by a "sandwich" ELISA using goat anti-human Ig (Cappel Labs) as the capture reagent, pooled human serum of known Ig concentration as the standard, and peroxidase-conjugated goat anti-human Ig as the detection reagent. Microplates (Dynatech) pre-coated with the capture reagent were incubated for three hours at room temperature with dilutions of SCID serum or the standard, extensively washed, and the detection reagent added. After peroxidase-catalyzed color development, the optical density at 490 nm was quantitated on a Biotek microplate reader.

There was a rapid increase in spontaneous human Ig secretion in recipients injected with $50 \times 10^6$ PBL regardless of the EBV status of the donor. The cause of this Ig production is not understood at present, but these data suggest that it is not necessarily related to EBV transformation of B cells (Aman, P., Ethlin-Henriksson, B. and Klein, G., *J. Immunol. Methods*, 87:119, 1986) and may not be abnormal since transfer of normal mouse lymphoid cells to SCID mice results in similar secretion of mouse Ig (unpublished observations). Transfer of smaller numbers of PBL resulted in a slower increase in human Ig levels. SCID recipients that survived long-term (currently sixteen to twenty-six weeks) showed stable levels of human Ig ranging from 0.1 to 1.0 mg ml$^{-1}$ (normal range of human serum Ig is 7–24 mg ml$^{-1}$), whereas recipients of higher numbers of PBL from EBV-seropositive donors continued to increase Ig production up to 5 mg ml$^{-1}$.

Figure 3A:
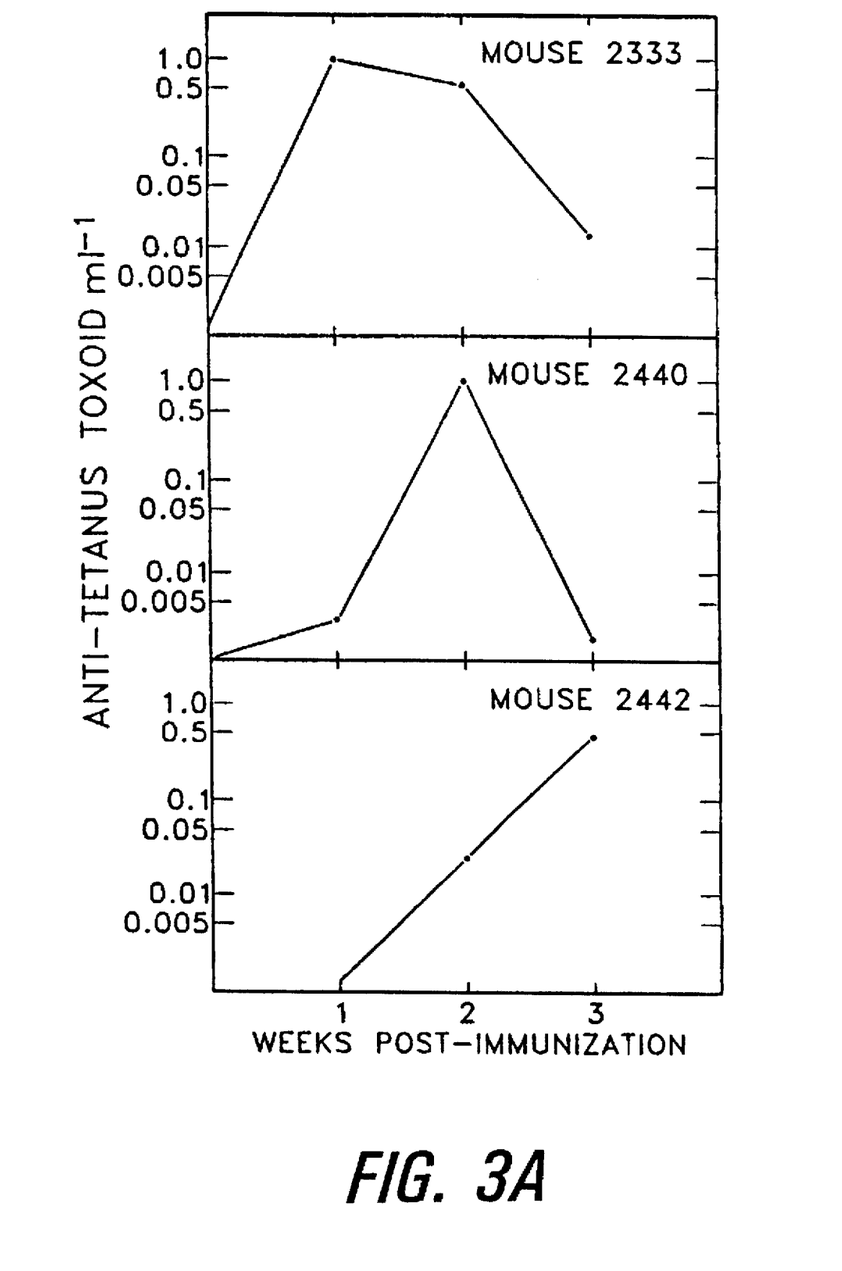
FIG. 3a presents the results of mice immunized within three weeks following transfer of PBL, showing tetanus toxoid-specific antibody levels in representative SCID mice immunized with tetanus toxoid following reconstitution with PBL.
Figure 3B:
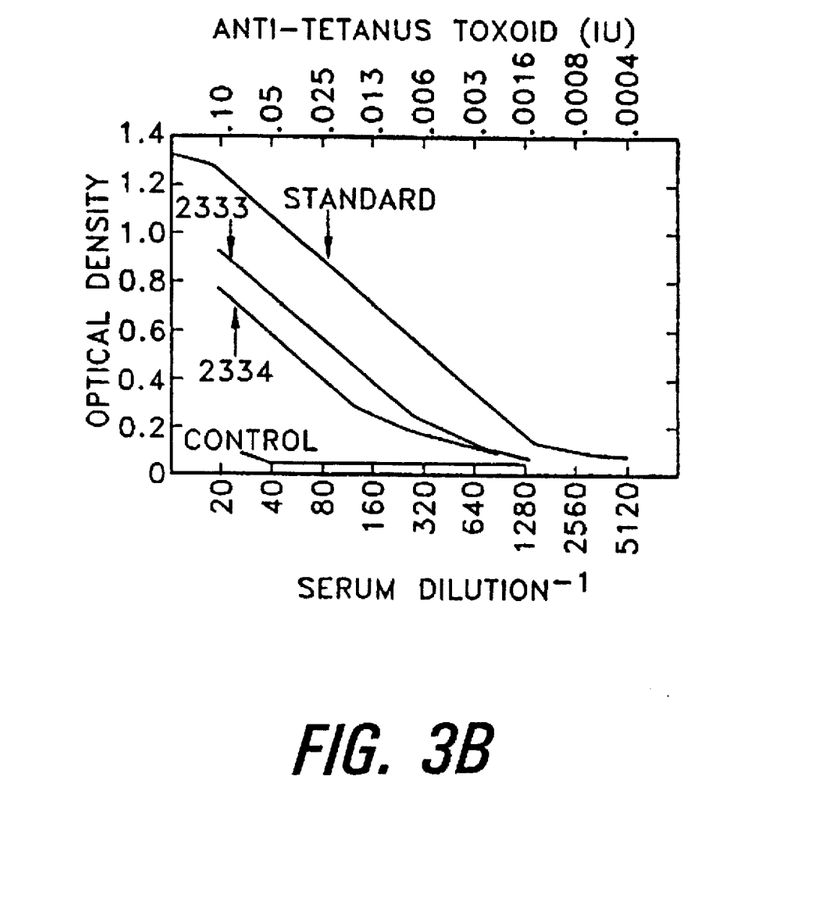
FIG. 3b shows that the serum of SCID mice at two weeks post-immunization gave titration curves parallel to that of the standard in an ELISA.

The demonstration that a functionally intact human immune system can survive in SCID recipients is of fundamental importance for the potential utility of the model. PBL-reconstituted SCID mice were immunized with tetanus toxoid, a protein antigen to which the PBL donors were known to be immune, and measured the antibody response one to three weeks later. FIG. 3 presents the results of mice immunized within three weeks following transfer to $50 \times 10^6$ PBL. Tetanus toxoid-specific antibody levels in representative SCID mice immunized with tetanus toxoid one (mice 2440 and 2442) or two (mice 2333 and 2334) weeks following reconstitution with $50 \times 10^6 \text{EBV}^+$ PBL. The selected data represent the three patterns of response seen in ten of twelve immunized animals. The selected data represent the three patterns of response seen in ten of twelve mice immunized i.p. with 100 Ig trinitrophenyl(TNP)-conjugated tetanus toxoid in phosphate buffered saline. Serum was collected prior to immunization and at weekly intervals thereafter. Antibodies to both TNP and tetanus toxoid were quantitated by ELISA. Only data for tetanus toxoid-specific antibodies are reported here. TNP-specific antibody was detected following immunization, but the lack of appropriate control antibodies made quantitation difficult. The tetanus toxoid-specific ELISA was a direct binding assay in which tetanus toxoid (Wyeth Labs) was bound to microplates, and the binding of SCID serum to the plates compared to hyperimmune anti-tetanus globulin (Hypertet, Cutter Labs) standardized to contain 250 IU ml$^{-1}$. After extensive washing the bound control and standard antibody was detected with peroxidase-conjugated goat anti-human Ig as described in FIG. 2. FIG. 3b illustrates the sensitivity of this ELISA and demonstrates that serum of SCID mice two weeks post-immunization gave titration curves parallel to that of the standard. The detection limit of the assay is about 0.003 IU ml$^{-1}$, so all data reported are well above this limit with the exception of the one and three week points on mouse 2440. The two PBL-reconstituted SCID mice immunized at twenty weeks post-transfer responded by producing 0.20 and 0.12 IU of antibody, respectively. For comparison, normal volunteers immunized with tetanus toxoid are reported to generate 8 to 16 IU of antibody using a similar ELISA (Farzad, Z., James, K. and McClelland, D. B. L., *J. Immunol. Methods,* 87:199, 1986).

Eight of ten animals produced detectable antibody to tetanus toxoid, with the earliest responders generally displaying the highest antibody titer. The amount of antibody found in responder mice ranged from 1 to 10% of the amount found in immunized humans (Farzad et al., ibid.). Two SCID recipients of $10 \times 10^6$ PBL were immunized at twenty weeks post-PBL reconstitution, and both of these mice produced antibody to tetanus toxoid at about 1% of the level of normal humans.

Figure 4:
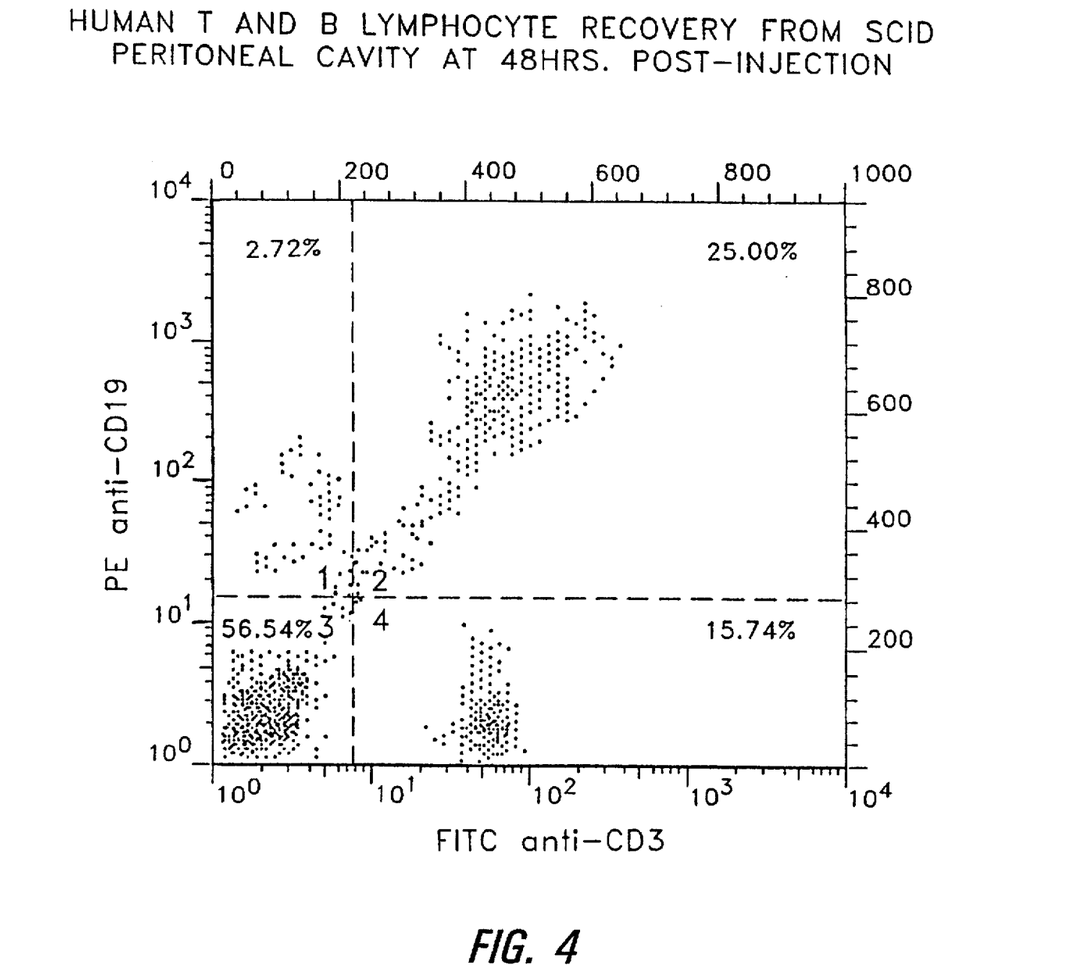
FIG. 4 shows the results of analysis of human lymphoid cells by flow cytometry using peritoneal cavity cells that were recovered from SCID mice injected 48 hours earlier with human PBL. The results show survival of human T cells (both CD4 and CD8 subsets) and B cells, and the activation of large cells which include both human and mouse cells. The large cells bind antibodies non-specifically, so their identification depends on alternative techniques such as in situ cytohybridization.

The results of analysis of human lymphoid cells by flow cytometry are shown in FIG. 4. Peritoneal cavity cells were recovered from SCID mice injected 48 hours previously with 50×10$^6$ human PBL. The cells were stained for 30 minutes with fluorescein- or phycoerythrin-conjugated monoclonal antibodies specific for CD3 (a pan-T cell marker) and CD19 (a B cell marker). Two color immunofluorescence was analyzed on a Becton-Dickinson FACS-CAN flow cytometer. The results indicate survival of a discrete population of small T cells (16% of total cells), a population of B cells; non-T, non-B cells which include mouse cells, and a mixed population of large, activated cells that non-specifically bind both antibodies. This artifactual staining of activated cells, which may be of either mouse or human origin, complicates enumeration of human cells for several weeks post-transplantation. However, at intervals of 12 weeks or more following PBL injection, fewer activated cells are present, and it is easier to identify surviving human T and B cells. T cells are present in the spleen and peritoneal cavity of these long-term recipients, and the majority of the T lymphocytes belong to the CD4 subset.

This experiment suggests that functional human antigen presenting cells, helper T cells, and B cells persist for at least twenty weeks in SCID recipients, although a role for murine antigen-presenting cells cannot be entirely excluded. Further evidence of functional reconstitution was obtained from culturing the spleen or peritoneal cells of PBL-reconstituted SCID mice with tetanus toxoid, phytohemagglutinin, or pokeweed mitogen. These antigens/mitogens stimulated increased thymidine incorporation in cells from most, but not all, recipients tested (data not shown), while unreconstituted SCID mice failed to respond to these stimuli.

While the greatest and most common and probably the most important applications of this invention will be the transfer of cells of the human immune system to laboratory animals of another species, most commonly mice such as SCID or nude mice, the invention can be used to study the immune system of any donor animal in a recipient animal of any other species which will, as explained above, accept the immune system cells, such as lymphocytic, myelocytic and erythrocytic lineage which are capable of developing immune functions, of the donor animal and permit such cells to flourish In vivo and produce the immune response of the donor animal in the recipient animal.

In addition, it has been established that such recipient laboratory animals injected with human immune system cells, such as lymphocytic, myelocytic and erythrocytic, e.g. leukocytes, are highly prone to the development of human lymphocyte malignancies, thus providing a rapid and attractive laboratory animal for the study of malignant transformation of normal human immune system organ cells. Malignancies observed to date have been of B cell origin, but T cell malignancies would also develop in this system. EBV, or other viral infections of cells, may be important in some forms of these malignant transformation events but the role of the presence or absence of an infecting virus has not been fully defined and data demonstrate that a virally infected cell is not essential.

The source of the cells, and the history of the cells, used to inject the laboratory SCID animal is not critical, if the cells carry the immunological characteristics of the donor. Thus, frozen, previously stimulated and other cells from the immune system of the donor may be used. As shown in the examples, human immune system cells, such as lymphocytic, myelocytic and erythrocytic lineage which are capable of developing immune functions, constitute one of the important sources of immune system transfer cells for use in this invention but the immune system of other animals may be studied according to this invention.

The immune system of the donor can be induced in the recipient using normal cells or cells which are defective or abnormal, e.g. from a patient with lupus erythematosus, whether or not the patient has malignancies. Malignancies can be induced in the recipient using non-malignant cells from the donor, whether or not normal.

A first step of enormous importance has been accomplished, revealing the creation of a system in which to test human immune responses in vivo in a laboratory animal. There are, of course, substantial questions to be resolved respecting the precise explanation of the phenomena which have been discovered, but the appreciation of the significance of the discovery need not await a full understanding of the biological mechanisms involved. For example, while it is presumed that functional human T and B lymphocytes in SCID mice are derived principally from long-lived recirculating mature cells, such reconstitution from recirculating stem cells or progenitors is perhaps another and/or better explanation.

The normal regulatory interactions that lead to homeostasis in the intact immune system appear to be altered in PBL-reconstituted SCID mice, resulting in spontaneous B cell activation in all recipients and tumor formation in recipients of high numbers of EBV$^+$ PBL. The role of human T cells responding to murine xenoantigens in these processes is undefined for the moment. The development of human B cell lymphomas in SCID recipients of high but not low numbers of PBL is a provocative finding, and is reminiscent of the development of EBV-positive lymphomas in human SCID patients receiving bone marrow transplants (Shearer, W. T. et al., N. Engl. J. Med., 312:1159, 1985). This outcome may reflect a low frequency of latent EBV infection in B cells (Tosato, G. et al., J. Clin. Invest., 73:1789, 1984), a rare transforming event, a B cell expansion that is proportional to the strength of the xenogeneic GVH reaction by T cells, or combinations of all these factors. Nonetheless, this observation of rapid development of B cell neoplasms provides an important new model for the study of human lymphomagenesis.

In initial studies of the reconstituted SCID mice with human cells, 10 to 100×10$^6$ Ficoll-Hypaque separated PBL from healthy adult male donors were injected either intraperitoneally (i.p.) or intravenously (i.v.) into SCID mice recipients.. Engraftment of human cells in all mice injected i.p. was observed but no evidence was observed of engraftment of PBL given i.v. Eight mice that received more than 40×10$^6$ PBL i.p. began to show evidence of clinical illness at 6–8 weeks post-transplantation, while four recipients of 10×10$^6$ PBL are alive and well over one year after injection. Necropsy of affected animals revealed the presence of numerous tumor masses in the peritoneal cavity, liver, lungs, and kidneys and diffuse enlargements of the spleen and peripheral lymph nodes. Histological examinations of these tumor masses revealed a lymphoblastic proliferation, and tumor DNA hybridized both with human Alu sequence probe and a probe specific for the internal repeat elements of EBV. Tumor cells were stained by antibodies to human immunoglobulin and to the B lymphocyte-specific markers CD19 and CD20. Both donors involved in these experiments were formed to be seropositive for antibodies to EBV.

Figure 5:
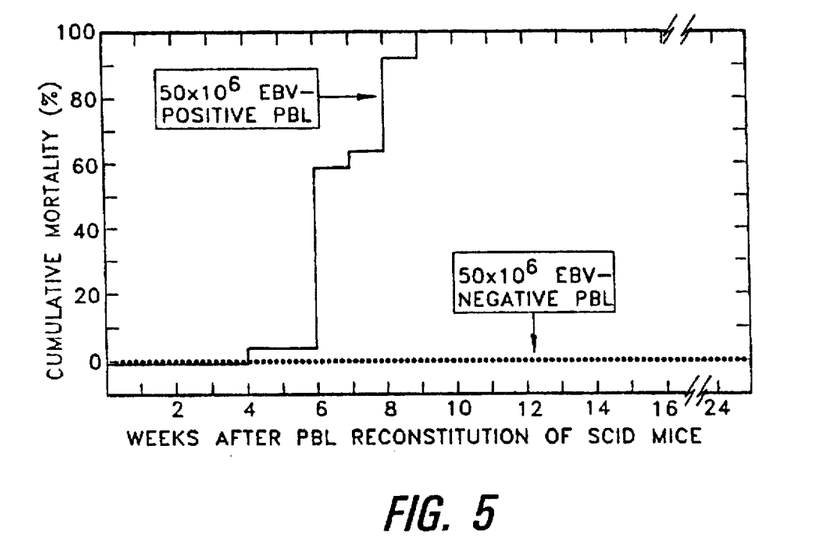
FIG. 5 shows the cumulative mortality of SCID mice from one to 24 weeks after receiving equivalent numbers of PBL from either EBV-positive or EBV-negative donors.

These data led to the postulation that prior EBV infection caused either a polyclonal or monoclonal B cell lymphoproliferative disease following transfer of sufficient numbers of PBL's to SCID mice. This hypothesis was tested by comparing the appearance of tumors in SCID mice receiving equivalent numbers of PBL's from either EBV-positive or EBV-negative donors. The results of the studies are presented in FIG. 5. These results indicate that EBV exposure is related to the development of these spontaneous lymphomas. Further data show that these tumors are often bi- or triclonal, and involve both IgM- and IgG-producing B cells, although IgM-positive tumors are more common.

The development of EBV-associated B cell lymphomas in SCID mice provides a new model for studying early steps in lymphomagenesis.

Figure 6:
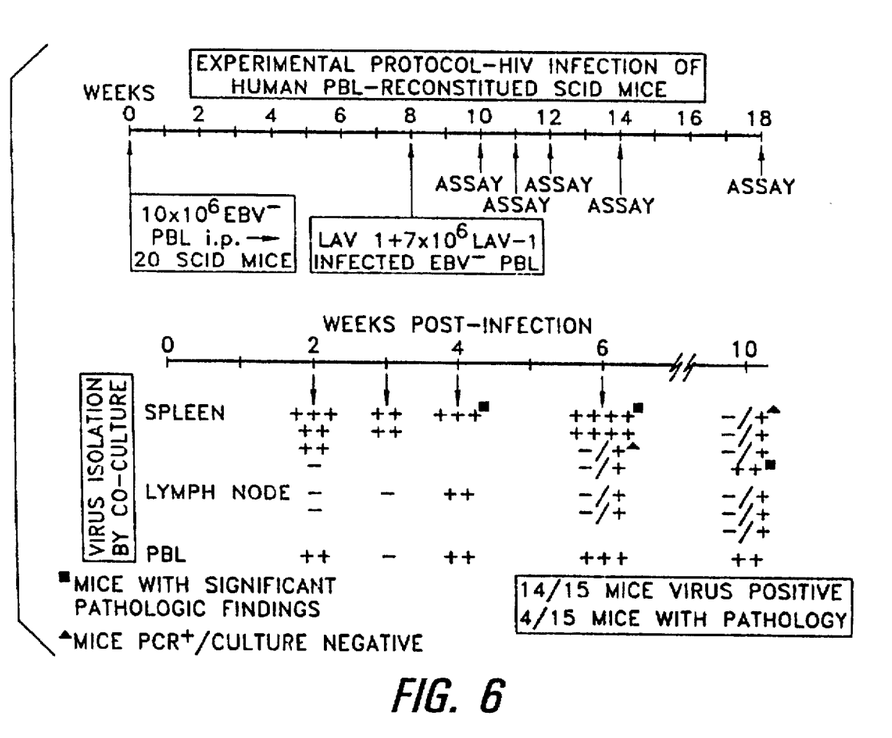
FIG. 6 shows the protocol and results in which SCID mice were reconstituted with PBL from an EBV-seronegative donor and infected 8 weeks later with the LAV-1 strain of HIV-1, from which HIV was recovered by virus culture.

SCID mice reconstituted with $10 \times 10^6$ PBL from an EBV-seronegative donor have been infected 8 weeks later with LAV-1 strain of HIV-1, given as a mixture of free virus and in vitro infected syngeneic T lymphoblasts. As shown by the data depicted in FIG. 6, HIV was recovered by virus culture from almost all of these mice. HIV replication was detected by co-cultivation of fresh human T lymphoblasts and cells from PBL-reconstituted SCID mice. Viral replication was quantitated by the appearance of p24 core protein in the culture supernatant using the Abbot p24 capture assay. Virus presence was confirmed by PCR and in situ hybridization. Moreover, four animals with very high levels of virus have developed AIDS-like syndrome characteristics by wasting, weight lost, and depletion of human T lymphocytes. Thus, a useful animal model for understanding the pathogenesis of AIDS has been developed.

While these observations raise many unresolved issues, what seems most remarkable is that these xenografts were successful in the first place. With further manipulation, it is believed that SCID mice reconstituted with human lymphoid cells can be made to mimic even more closely the intact human immune system. Means are thus provided for predicting human immune responses to vaccines, for testing immunomodulators, and for exploring pathogenic mechanisms in HIV infection and human neoplasia.

The invention will be recognized as being of broad scope with specific applications and advantages in the study of the human immune system but is not limited to such studies or to the specifics set forth hereinbefore.

INDUSTRIAL APPLICATION

This invention is useful in conducting immunological research, providing laboratory animals and methods which are useful in evaluating diagnostic materials and devices and in evaluating chemical and biological agents for therapeutic applications in humans and animals.

What is claimed is:

1. A scid/scid mouse, modified by injection of non-malignant mature peripheral leukocytes of a human donor into said mouse, wherein said modified mouse comprises human leukocytes proliferated in vivo in the mouse and exhibits an immune response which is characteristic of said human donor upon stimulation with an immunogen, and wherein said immune response comprises production of human antibodies.

2. The mouse of claim 1, which is further modified by infection with human immunodeficiency virus.

3. The mouse of claim 1, wherein said human antibodies are monoclonal antibodies.

4. A method of modifying a scid/scid mouse, comprising the steps of:
   injecting non-malignant mature peripheral leukocytes of a human donor into said mouse; and
   maintaining said mouse alive for a period of two or more weeks sufficient for said leukocytes to proliferate in vivo in said mouse, thereby causing said modified mouse to exhibit an immune response which is characteristic of said human donor upon stimulation with an immunogen, and wherein said immune response comprises production of human antibodies.

5. The method of claim 4, further comprising the step of infecting said modified mouse with human immunodeficiency virus.

6. The method of claim 4, wherein said human donor is a carrier of Epstein-Barr virus, and further comprising the step of maintaining said modified mouse alive until tumors are induced as a result of the presence of Epstein-Barr virus.

7. The method of claim 4, wherein said modified mouse produces human monoclonal antibodies upon stimulation with an immunogen.

8. The method of claim 6, wherein said modified mouse produces human monoclonal antibodies upon stimulation with an immunogen.

9. The method of claim 4, wherein said modified mouse is used in manufacturing of human monoclonal antibodies.

10. The method of claim 6, wherein said modified mouse is used in manufacturing of human monoclonal antibodies.

11. A method of modifying a scid/scid mouse, comprising the steps of:
    injecting myelocytic, lymphocytic or erythrocytic lineage cells of a human donor into said mouse; and
    maintaining said mouse alive for a period of two or more weeks sufficient for said myelocytic, lymphocytic or erythrocytic lineage cells to proliferate in vivo in said mouse, thereby causing said modified mouse to exhibit an immune response which is characteristic of said human donor upon stimulation with an immunogen.

* * * * *